United States Patent [19]

Hardy et al.

[11] 4,394,330
[45] Jul. 19, 1983

[54] PHOSPHONATE DERIVATIVES OF POLYALKYLENE POLYAMINES AS FLAME RETARDANTS

[75] Inventors: Thomas A. Hardy, Tarrytown, N.Y.; Sophia Y. Liu, Freemont, Calif.

[73] Assignee: Stauffer Chemical Company, Westport, Conn.

[21] Appl. No.: 125,591

[22] Filed: Feb. 28, 1980

Related U.S. Application Data

[63] Continuation of Ser. No. 959,390, Nov. 9, 1978, abandoned, which is a continuation of Ser. No. 755,278, Dec. 29, 1976, abandoned.

[51] Int. Cl.³ .......................... C07F 9/40; C08G 18/00
[52] U.S. Cl. ...................................... 260/932; 521/169
[58] Field of Search ........................................ 260/932

[56] References Cited

U.S. PATENT DOCUMENTS 2,248,729  7/1941  Ulrich et al. .................... 260/584

Primary Examiner—Anton H. Sutto
Attorney, Agent, or Firm—Roger S. Benjamin

[57] ABSTRACT

Flame retardant phosphonate derivatives of polyalkylene polyamines are prepared having the structural formula:

$$\left[ (R^4O)_2\overset{O}{\underset{\|}{P}}R^3 \right]_m \underset{(HOR^5)_{2-m}}{\diagdown} N - \left[ R^1 - \underset{\underset{y}{|}}{\overset{X}{N}} \right]_y R^2 - N \underset{\left[ R_3\overset{O}{\underset{\|}{P}} - (OR^4)_2 \right]_n}{\diagup}^{(R^5OH)_{2-n}}$$

wherein
$R^1$, $R^2$ and $R^5$ can be the same or different substituted or nonsubstituted lower alkylene groups of about 2–10 carbons, or aryl groups of about 6–14 carbons; and $R^5$ can also be haloalkyl of about 1–10 carbons;
$R^3$ can be a lower alkylene radical of about 1–10 carbons;
$R^4$ can be an alkyl, alkenyl, alkynyl, or aryl group of about 1–20 carbons;
m is a number from 0 to 2;
n is a number from 0 to 2;
y is a number from 0 to 10; and
x can be the same as the ($R^5$OH) group or the $$\left[ R^3\overset{O}{\underset{\|}{P}} - (OR^4)_2 \right] \text{ group}$$

The preparation involves the condensation of a polyalkylene-polyamine with an aldehyde or ketone and a phosphonate or a phosphite. The condensation product is then reacted with an epoxide to yield the phosphonate derivatives of polyalkylene-polyamines.

1 Claim, No Drawings

PHOSPHONATE DERIVATIVES OF POLYALKYLENE POLYAMINES AS FLAME RETARDANTS

This is a continuation, of application Ser. No. 959,390 filed Nov. 9, 1978, now abandoned, which is a continuation of Ser. No. 755,278, filed Dec. 29, 1976, now abandoned.

BACKGROUND OF THE INVENTION

1. Field of the Invention

The present invention relates to novel phosphonate derivatives of polyalkylene-polyamines, methods of preparation and methods of use as flame retardants in polyurethane foams, plastics, textiles and cellulose.

2. The Prior Art

The phosphonate derivatives of polyalkylene-polyamines according to the present invention are novel. Prior art compositions of interest include polyphosphonate ester derivatives of diamines disclosed in U.S. Pat. Nos. 2,635,112; 2,870,190; 3,036,108; and 3,551,527. These compositions have the general formula:

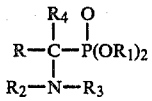

wherein R, $R_1$, $R_2$, $R_3$, and $R_4$ can be the same or different substituted or nonsubstituted organic radicals.

Also known are polyphosphonic acid derivatives of diamines as disclosed in published U.S. Application B265,369. Moreover, polyphosphonate ester derivatives of monoamines with hydroxyalkyl groups are described in U.S. Pat. Nos. 3,548,038 and 3,555,124.

SUMMARY OF THE INVENTION

In accordance with the present invention, novel phosphonate derivatives of polyalkylene-polyamines are prepared. These derivatives have the structural formula:

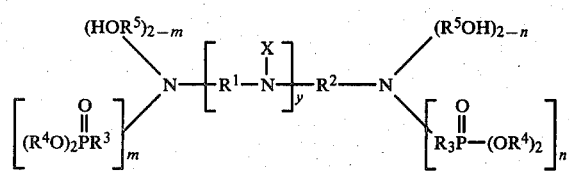

wherein $R^1$, $R^2$ and $R^5$ can be the same or different substituted or nonsubstituted lower alkylene groups of about 2–10 carbons, or aryl groups of about 6–14 carbons; and $R^5$ can also be haloalkyl of about 1–10 carbons;

$R^3$ can be a lower alkylene radical of about 1–10 carbons $R^4$ can be an alkyl, alkenyl, alkynyl, or aryl group of about 1–20 carbons;

m is a number from 0 to 2;

n is a number from 0 to 2; and y is a number from 0 to 10; and

X can be the same as the ($R^5$OH) group or the

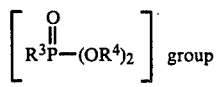

group

The phosphonate derivatives of polyalkylene-polyamines of the present invention are synthesized according to the reaction scheme:

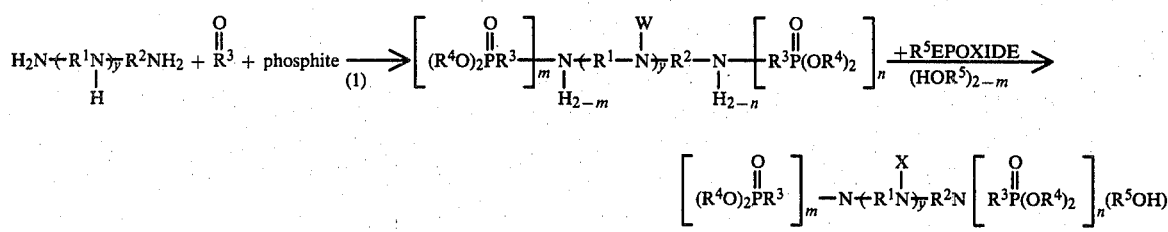

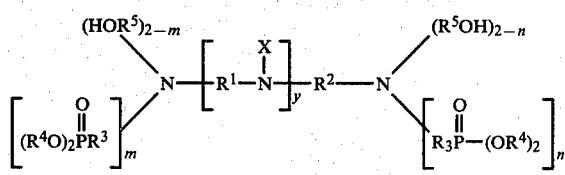

wherein phosphite has the structure $(R^4O)_2P(O)H$ or $(R^4O)_3P$; $R^1$, $R^2$, $R^3$, $R^4$, $R^5$, m, n, y, and X are defined above and W is hydrogen or

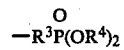

The reaction scheme can be described as condensation of a polyalkylene-polyamine with an aldehyde or ketone and a phosphonate or phosphite. An epoxide is then reacted with the condensation product to yield the novel derivatives of the present invention.

Derivatives of polyalkylene-polyamines of the present invention are excellent flame retardants for polyurethane foams and can also be utilized as flame retardants for plastics, textiles and cellulose.

DETAILED DESCRIPTION OF THE INVENTION

In the phosphonate derivatives of polyalkylene-polyamines of the present invention having the structural formula:

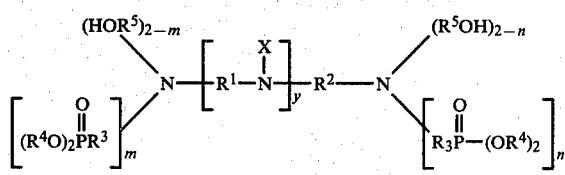

wherein $R^1$, $R^2$, $R^3$, $R^4$, $R^5$, m, n, y and X are as defined above. Exemplary $R^1$, $R^2$, and $R^5$ groups include but are not limited to ethylene, propylene, isopropylene, butylene, tert-butylene, and phenylene. Additionally, $R^5$ groups can include but are not limited to chloroethylene, chloropropylene and trichlorobutylene.

Exemplary $R^3$ groups include but are not limited to methylene, ethylene, propylene, isopropylene, methylmethylene, dimethyl methylene, benzal and furfural.

Exemplary $R^4$ groups include but are not limited to methyl, ethyl, propyl, isopropyl, allyl, butyl, pentyl and phenyl.

Exemplary phosphite reactants include but are not limited to:

  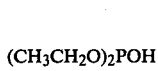

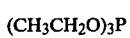  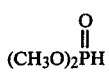

  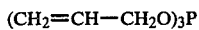

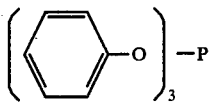  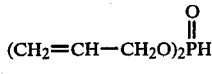

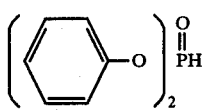

The method of preparing the derivatives of the present invention comprises contacting a polyalkylene-polyamine reactant having the structural formula:

$$H_2N(R^1N)_yR^2NH_2 \quad\quad (II)$$
$$\quad\quad\quad\; H$$

wherein $R^1$, $R^2$ and y are as defined above; with an aldehyde reactant having the structural formula:

$$\underset{R^3}{\overset{O}{\|}} \quad\quad (III)$$

wherein $R^3$ is as defined above; and a phosphite reactant having one of the structural formulas:

$$(R^4O)_2\text{-P(O)H} \quad\quad (IV)$$

$$(R^4O)_3P \quad\quad (V)$$

wherein $R^4$ is as defined above.

The reaction product is then reacted with an epoxide reactant having a structural formula such as:

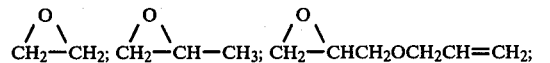

among others.

The polyalkylene polyamine reactants which are suitable in the present invention include, among others, ethylene diamine, diethylene triamine, triethylenetetramine, tetraethylene pentamine, n-aminoethylpiperazine, piperazine, melamine, 1,4-phenylene diamine and 1,3-phenylenediamine.

Suitable aldehyde and ketone reactants include, among others, formaldehyde, acetaldehyde, propionaldehyde, butyraldehyde, furfural, acetone, methyl ethyl ketone and benzaldehyde.

The phosphonate or phosphite reactants used in this synthesis can be, among others, di-alkyl or tri-alkyphosphites, or the corresponding aryl compounds; dimethylphosphite, diethylphosphite, methyl ethyl phosphite, dipropylphosphite, dibutyl phosphite, dioctyl phosphite, bis-chloroethyl phosphite, diphenylphosphite, trimethyl phosphite, triethyl phosphite, tripropyl phosphite, triphenyl phosphite and trioctyl phosphite.

Suitable epoxide reactants include, among others, ethylene oxide, propylene oxide, butylene oxide, glycidyl ethers, epichlorohydrin, trichlorobutylene oxide and other halogenated epoxides.

The following equation (1) is representative of the reaction:

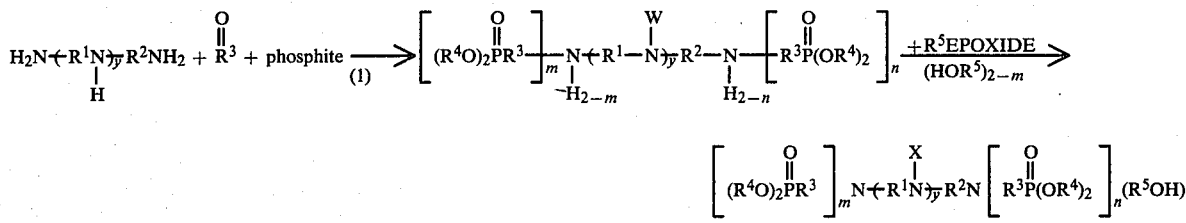

wherein phosphite, $R^1$, $R^2$, $R^3$, $R^4$, $R^5$, m, n, y, W, and X are as defined above.

The stoichiometry of the foregoing reaction (1) can be adjusted by one skilled in the art so that the final phosphorus content and degree of hydroxyl functionality meets a desired specification.

The compositions of the present invention are prepared by first preparing an intermediate according to equation (1). This is accomplished by contracting the polyalkylene-polyamine, aldehyde and phosphite reactants in a suitable reaction vessel. Two of the three reactants are generally contacted first at a temperature from about 0° C. to about 80° C. followed by addition of the third reactant at a temperature from about 0° C. to about 120° C. The addition of the third reactant generally results in an exothermic reaction which can be controlled by conventional heat transfer equipment to prevent the reaction from becoming too hot.

The epoxide reactant is then added to the intermediate to complete the preparation of the compounds of the present invention. This addition also results in an exothermic reaction and the temperature can also be controlled with the heat transfer equipment. Addition of the epoxide is generally conducted at a temperature from about 0° C. to about 120° C.

The reactions according to equation (1) can be carried out in conventional equipment provided with a stirring or mixing apparatus. Efficient stirring is necessary, especially when solid paraformaldehyde is used or when no solvent is used. This is due to a viscosity buildup.

Washing of the products is optional. The solvent, unreacted starting materials and other volatiles can be removed under reduced pressure.

Identification of the products can be accomplished by determination of hydroxylnumber, %P, %N, infrared and nuclear magnetic resonance spectroscopy or gas, liquid and column chromatography. Typical yields of the products are from about 40% to about 95%.

The flame retarded polyurethanes of the present invention can be prepared by utilizing any of the conventional basic catalysts such, for example, as N-methyl morpholine, N-ethyl morpholine, 1,2,4-trimethylpiperazine, trimethyl amine, triethyl amine, tributyl amine and other trialkyl amines, the esterification product of adipic acid and diethylethanolamine, triethyl amine citrate, 3-morpholinopropionamide, 1,4-bis (2-hydroxypropyl) -2-methylpiperazine, 2-diethylaminoacetamide, 3-diethylaminopropionamide, diethylethanolamine, triethylenediamine, N,N,N',N'-tetrakis (2-hydroxypropyl) ethylenediamine, N,N'-dimethylpiperazine, N,N-dimethylhexahydroaniline, tribenzylamine and sodium phenolate. Said catalysts are generally used in amounts of about 0.01 to 5% by weight. Also, applicable are tin compounds, e.g. hydrocarbon tin acrylates such as dibutyltin dilaurate, dibutyltin diacetate, dibutyltin dioctoate, tributyltin monolaurate, dimethyltin diacetate, diocyltin diacetate, dilauryltin diacetate, dibutyltine maleate, hydrocarbon tin alkoxides, e.g. dibutyltin diethoxide, dibutyltin dimethoxide, diethyltin dibutoxide as well as other tin compounds, e.g. octylstannoic acid, trimethyltin hydroxide, trimethyltin chloride, triphenyltin hydroxide, trimethyltin chloride, triphenyltin hydride, triallyltin chloride, trioctyltin fluoride, dibutyltin dibromide, bis-(carbonethoxymethyl) tin diiodide, tributyltin chloride, trioctyltin acetate, butyltin trichloride, octyltin tris(thiobutoxide), dimethyltin oxide, dibutyl tin oxide, dioctyltin oxide, dphenyltin oxide, stannous octanoate, and stannous oleate. Said tin compounds are generally used in amounts of about 0 to about 5% by weight.

Any of the conventional surfactants can be used in amounts of about 0.01 to 2% or less, e.g. 0.2% by weight of the composition. The preferred surfactants are silicones, e.g. polydimethyl siloxane have a viscosity of 3 to 100 centistokes, triethoxydimethyl polysiloxane, molecular weight 850 copolymerized with a dimethoxypolyethylene glycol having a molecular weight of 750.

The foaming reaction can, for example, be carried out by adding water to a polyol prior to or simultaneously with a surfactant, an isolyanate and a foaming or blowing agent. The foaming or blowing agent is usually a liquefied, halogen substituted alkane such, for example, as methylene chloride. Expecially preferred are those halogen substituted alkanes having at least one fluorine atom in their molecules such as trichlorofluromethane, dichlorodifluoromethane, dichloromonofluoromethane, chlorodifluoromethane, dichlorotetrafluoroethane, chlorodifluoromethane, dichlorotetrafluoroethane. These blowing agents are uniformly distributed in either the polyol reactant or the polyisocyanate reactant whereupon the reactants are mixed permitting the temperature of the mixture to rise during the ensuing reaction above the boiling point of the liquefied gas so as to produce a porous polyurethane. The water can be present in amounts from about 0–5% and the blowing agent in amounts from about 0–20% provided that at least about 0.1% of one or the other is utilized.

The flame retardant derivatives of polyalkylenepolyamines of the present invention are added to the foam reaction mixture in an amount from about 1% to about 20% by weight of said mixture.

EXAMPLES

EXAMPLE I

A 2 liter flask was charged with 103 g. of diethylene triamine and 515 g. of triethyl phosphite. The mixture was heated to 70° C. and with vigorous stirring 100 g. of paraformaldehyde was added slowly. Ice cooling was utilized to control the reaction exotherm and maintain the reaction temperature between 68° C. and 75° C. When the reaction exotherm subsided, 90 g. of ethylene oxide was added while the reaction temperature was maintained at 70° C.±5° C. The solvent was removed through a wipe film still at 90°–105° C. and 1 to 2 mmHg. The yield was 610 g. (95% yield) of

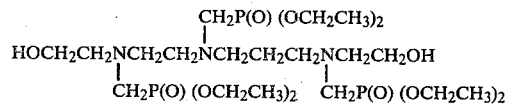

which was found to have a phosphorus content of 15.0% (theoretical was 14.5%), a nitrogen content of 6.7% (theorectical was 6.5%) and an acid number of 1.0 mg KOH/g.

EXAMPLE II

A one liter flask was fitted with an addition funnel, mechanical stirrer, thermometer and condenser. The flask was then charged with 200 ml. of n-propanol and 90 g. of paraformaldehyde. N-aminoethylpiperazine (129 g.) was then added dropwise at 40°–60° C. Following this, 498 g of triethylphosphite was added dropwise at 90°–95° C. The solution was heated to 90° C. and maintained at that temperature for 12 hours. Propanol and unreacted triethyl phosphite were then removed by wipe film distillation at 90° C. and 0.5 mmHg.

The residue (507 g.) was then treated with ethylene oxide at 60° C. for 10 hours. After wipe film removal of volatiles, a brown oil (476 g.) was obtained. The oil had an acid number of 5 mg KOH/g. and a hydroxyl number of 87 mg KOH/g. It contained 14.7% phosphorus and had a molecular weight of 470. The approximate structure was:

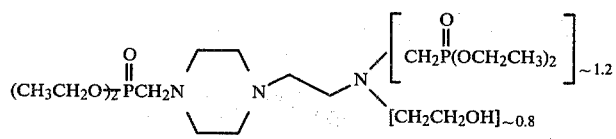

EXAMPLE III

A 3 liter, 3 necked flask was fitted with an addition funnel, magnetic stirrer, thermometer and condenser. The flask was charged with 324 g. of 37% aqueous formaldehyde and 90 g. of ethylene diamine. The solution was cooled to 10° C. with an ice bath and 552 g. of diethyl phosphite was added at 8°–11° C. The solution was gradually warmed to 100° C. and was maintained at that temperature for 1½ hours.

The solution was allowed to stand overnight, after which the material was neutralized with aqueous potassium hydroxide and extracted with benzene. The solvent was then removed by wipe film distillation giving a light yellow oil containing 16.4% phosphorus and 6.1% nitrogen. The product obtained had the structure:

(CH₃CH₂O)₂PCH₂NHCH₂CH₂NHCH₂P(OCH₂CH₃)₂

EXAMPLE IV

A one liter, 3 necked flask was fitted with a dropping funnel, stirrer, thermometer and condenser and was charged with 110 g. diethyl phosphite. With ice cooling, 21.6 g. of p-phenylene diamine was added slowly followed by addition of 64.8 g. of 37% aqueous formaldehyde. After that addition was complete, the reaction mixture was heated to 100° C. and held at that temperature for 45 minutes.

The reaction mixture was allowed to cool and was then neutralized with aqueous potassium hydroxide. The mixture was then extracted with benzene. The benzene extracts were dried over K₂CO₃ and evaporated to give 68.5 g. of a viscous brown oil corresponding to the structure:

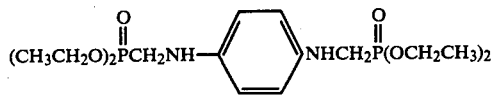
(CH₃CH₂O)₂PCH₂NH—⟨ ⟩—NHCH₂P(OCH₂CH₃)₂

EXAMPLE V

A rigid urethane foam was prepared by mixing the following componeents:

|  | Wt % |
|---|---|
| BE 375 (Aromatic Polyol) | 36.0 |
| DC 193 (Silicone Surfactant) | 0.5 |
| TMBDA (Amine Catalyst) | 0.35 |
| WATER | 0.35 |
| Fluorocarbon 11B (Blowing Agent) | 9.0 |
| Product of Example I | 8.5 |

This mixture was then admixed with 49.8% by weight of the total mixture of a polymeric isocyanate.

The resulting foam had a limiting oxygen index of 23.3 compared with 19–20 for a non-flame retarded foam.

EXAMPLE VI

A flexible polyurethane foam was prepared in a manner similar to that in Example V. A trifunctional polyol having a molecular weight of about 3700, a hydroxyl number of 46 and containing propanoxide and ethylene oxide was utilized with a stannous octoate catalyst. At 12 phr. of the flame retardant of Example 1, the foam was self extinguishing.

What is claimed is:

1. A composition having the structural formula:

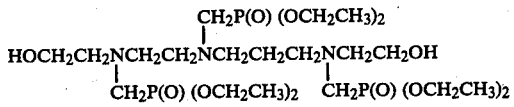

HOCH₂CH₂NCH₂CH₂NCH₂CH₂CH₂NCH₂CH₂OH with CH₂P(O)(OCH₂CH₃)₂ substituents

* * * * *

UNITED STATES PATENT AND TRADEMARK OFFICE
CERTIFICATE OF CORRECTION

PATENT NO. : 4,394,330

DATED : July 19, 1983

INVENTOR(S) : Thomas A. Hardy, Sophia Y. Liu

It is certified that error appears in the above-identified patent and that said Letters Patent are hereby corrected as shown below:

Column 2, line 28, the right hand terminal part of the formula printed as "$(R^5OH)$" should be -- $(R^5OH)_{2-n}$ --.

Column 4, line 36, the right hand terminal part of the formula printed as "$(R^5OH)$" should be -- $(R^5OH)_{2-n}$ --.

Column 5, line 27, "dibutyltine" should be -- dibutyltin --.

Column 5, line 37, "dphenyltin" should be -- diphenyltin --.

Column 5, line 50, "isolyanate" should be -- isocyanate --.

Column 6, line 34, "theorectical" should be -- theoretical --.

Column 8, line 10, "componeents" should be -- components --.

Column 8, line 31, "propanoxide" should be -- propylene oxide --.

Signed and Sealed this

Thirteenth Day of March 1984

[SEAL]

Attest:

GERALD J. MOSSINGHOFF

*Attesting Officer*  *Commissioner of Patents and Trademarks*